(12) United States Patent
Fischer

(10) Patent No.: US 9,498,357 B2
(45) Date of Patent: Nov. 22, 2016

(54) STENT

(71) Applicant: Variomed AG, Balzers (LI)

(72) Inventor: Harald Fischer, Weingarten (DE)

(73) Assignee: VARIOMED AG, Balzers (LI)

( * ) Notice: Subject to any disclaimer, the term of this patent is extended or adjusted under 35 U.S.C. 154(b) by 0 days.

(21) Appl. No.: 14/439,212

(22) PCT Filed: Oct. 14, 2013

(86) PCT No.: PCT/EP2013/071407
§ 371 (c)(1),
(2) Date: Apr. 28, 2015

(87) PCT Pub. No.: WO2014/067770
PCT Pub. Date: May 8, 2014

(65) Prior Publication Data
US 2015/0290003 A1 Oct. 15, 2015

(30) Foreign Application Priority Data
Nov. 5, 2012 (DE) .................. 10 2012 220 129

(51) Int. Cl.
*A61F 2/915* (2013.01)
*A61F 2/90* (2013.01)
(Continued)

(52) U.S. Cl.
CPC .............. *A61F 2/90* (2013.01); *A61F 2/844* (2013.01); *A61F 2/91* (2013.01); *A61F 2/915* (2013.01); *A61F 2002/825* (2013.01); *A61F 2002/91566* (2013.01)

(58) Field of Classification Search
CPC .......... A61F 2/06; A61F 2/82; A61F 2/2002; A61F 2/915
See application file for complete search history.

(56) References Cited

U.S. PATENT DOCUMENTS 5,104,404 A  4/1992 Wolff
5,449,373 A * 9/1995 Pinchasik ............... A61F 2/856
                                                            606/198
(Continued)

FOREIGN PATENT DOCUMENTS

DE   197 49 691 A1   4/1999
EP   0 364 787 B1    3/1992
(Continued)

OTHER PUBLICATIONS

International Search Report mailed Jan. 3, 2014, from International Application No. PCT/EP2013/071407 (6 pages).
(Continued)

*Primary Examiner* — Suzette J Gherbi
(74) *Attorney, Agent, or Firm* — Kilpatrick Townsend & Stockton LLP

(57) ABSTRACT

The disclosed stent comprises at least two support portions and at least one connecting portion which follow one another in the longitudinal direction of the stent. Each support portion has multiple openings in the wall of the tubular body and border elements which are formed by the tubular body and which surround the openings and together with said openings form support portion cells in the expanded state. Two support portions which are adjacent to each other in the longitudinal direction are connected via a connecting portion lying between said support portions, and each of the mutually facing end faces of the adjacent support portions are formed by a row of end-face cells of the respective support portion. The connecting portion comprises connecting elements which are formed by the tubular body and which connect the mutually facing end faces of the two adjacent support portions.

18 Claims, 5 Drawing Sheets

Figure 1:
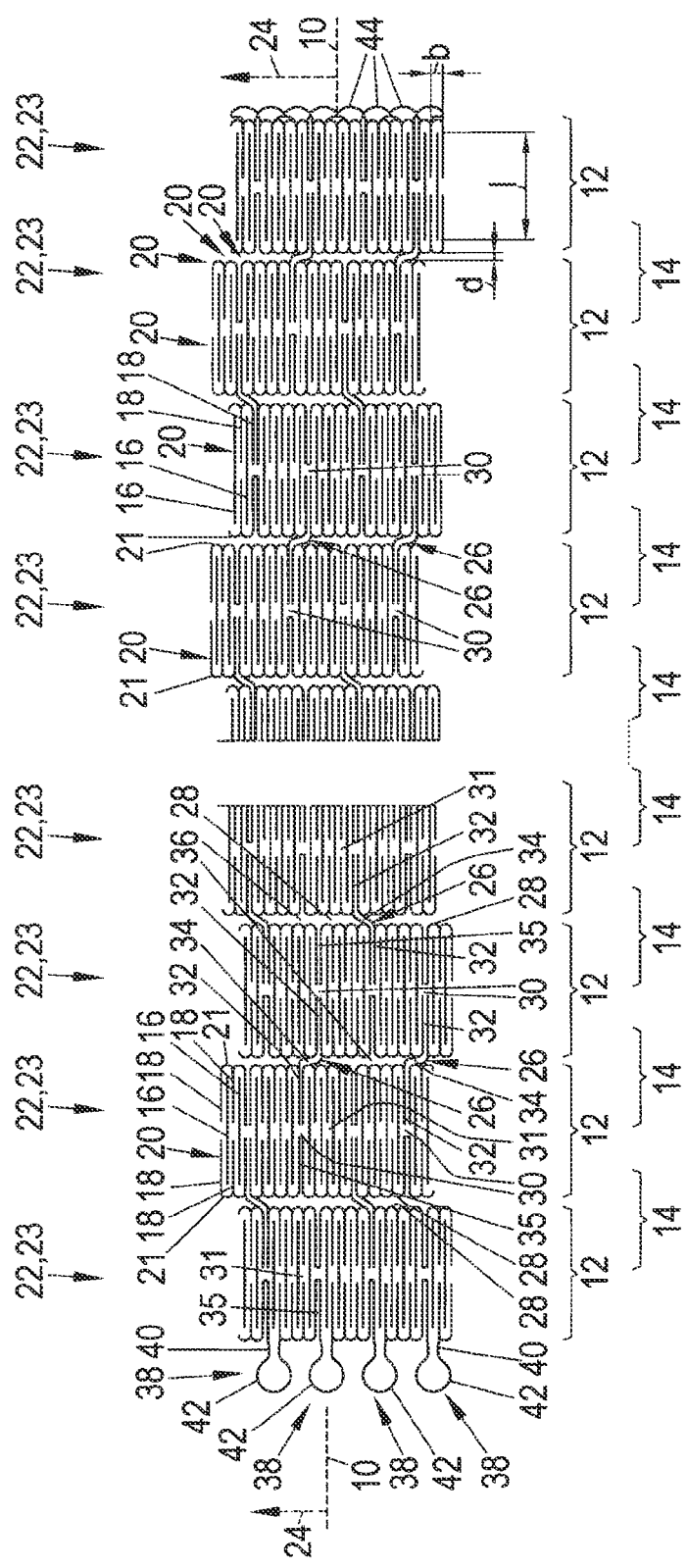

(51) Int. Cl.
*A61F 2/91* (2013.01)
*A61F 2/844* (2013.01)
*A61F 2/82* (2013.01)

(56) References Cited

U.S. PATENT DOCUMENTS

| | | | |
|---|---|---|---|
| 5,879,381 A | 3/1999 | Moriuchi et al. | |
| 5,938,697 A * | 8/1999 | Killion | A61F 2/91 623/1.15 |
| 6,159,238 A * | 12/2000 | Killion | A61F 2/91 128/898 |
| 6,355,057 B1 | 3/2002 | DeMarais et al. | |
| 8,882,829 B2 * | 11/2014 | Gladdish, Jr. | A61F 2/915 623/1.15 |
| 2002/0123792 A1 | 9/2002 | Burgermeister | |
| 2003/0144729 A1 * | 7/2003 | Bicek | A61F 2/91 623/1.16 |
| 2003/0195616 A1 * | 10/2003 | Pinchasik | A61F 2/856 623/1.16 |
| 2008/0097571 A1 | 4/2008 | Denison et al. | |
| 2008/0208319 A1 * | 8/2008 | Rabkin | A61F 2/91 623/1.16 |
| 2008/0275537 A1 | 11/2008 | Limon | |
| 2009/0076590 A1 * | 3/2009 | Keating | A61F 2/91 623/1.16 |
| 2009/0228088 A1 * | 9/2009 | Lowe | A61F 2/91 623/1.2 |
| 2011/0160843 A1 * | 6/2011 | Meyer | A61F 2/915 623/1.16 |
| 2011/0184507 A1 | 7/2011 | Fischer, Jr. et al. | |
| 2011/0224778 A1 * | 9/2011 | Gale | A61F 2/91 623/1.16 |
| 2012/0136428 A1 * | 5/2012 | Kveen | A61F 2/91 623/1.16 |
| 2012/0165921 A1 * | 6/2012 | Casey | A61F 2/915 623/1.16 |
| 2013/0060321 A1 * | 3/2013 | Kao | A61F 2/91 623/1.16 |
| 2013/0218260 A1 * | 8/2013 | Schlun | A61F 2/91 623/1.16 |
| 2013/0289707 A1 * | 10/2013 | Shanley | A61F 2/88 623/1.16 |

FOREIGN PATENT DOCUMENTS

| | | |
|---|---|---|
| EP | 0 540 290 A2 | 5/1993 |
| EP | 0 734 698 A2 | 10/1996 |
| EP | 0832618 A1 | 4/1998 |
| EP | 2 604 230 A1 | 6/2013 |
| FR | 2 758 253 A1 | 7/1998 |
| WO | 96/03092 A1 | 2/1996 |
| WO | 99/12495 A1 | 3/1999 |
| WO | 2012035550 A2 | 3/2012 |

OTHER PUBLICATIONS

International Preliminary Report on Patentability mailed Nov. 13, 2014, from International Application No. PCT/EP2013/071407 (22 pages).

* cited by examiner

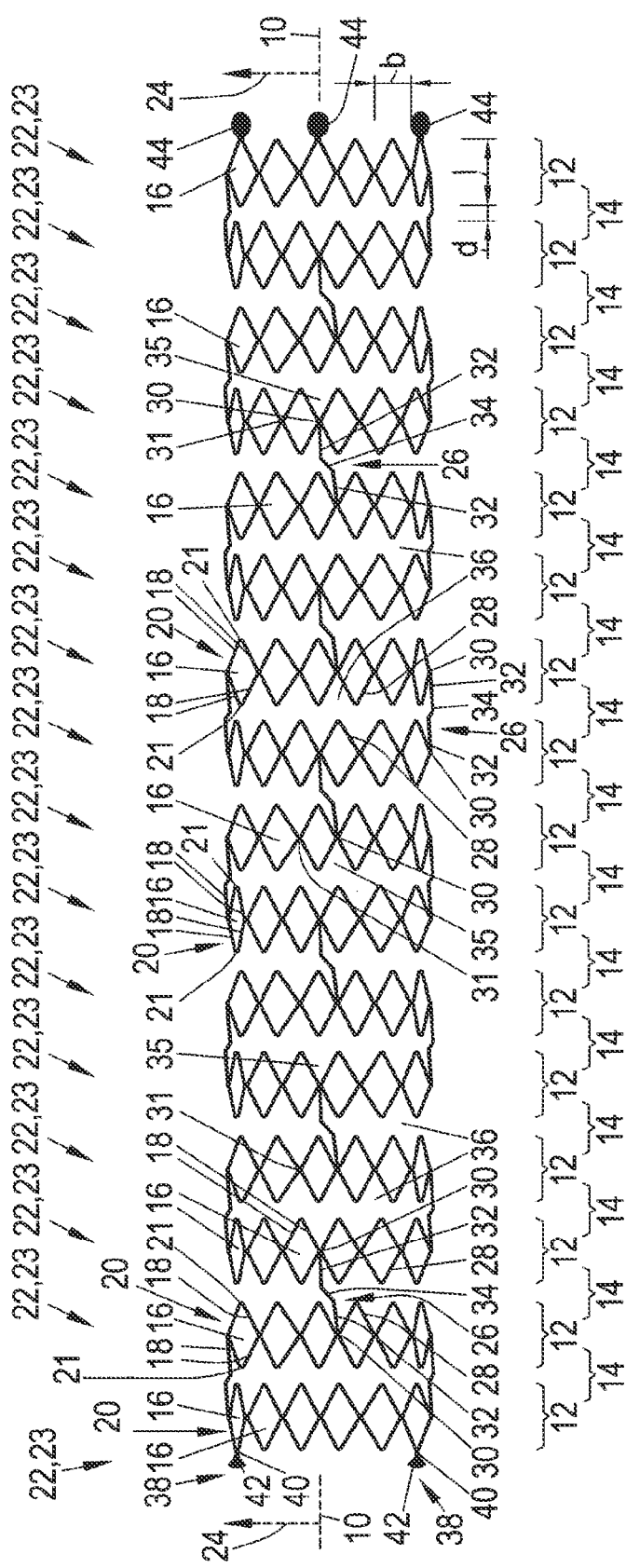
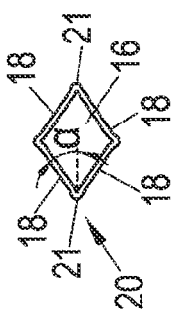
Fig.2
Fig.3

STENT

This application is a U.S. National Phase of International Application No. PCT/EP2013/071407, filed Oct. 14, 2013, which claims priority to German Patent Application No. 102012220129.7, filed Nov. 5, 2012, the disclosures of which are incorporated by reference herein.

The present invention relates to a stent for transluminal implantation into hollow organs, in particular into veins or generally into blood vessels, ureters, esophagi, the colon, the duodenum or the biliary tract, having a substantially tubular body which can be converted from a compressed state having a first cross-sectional diameter into an expanded state having an enlarged second cross-sectional diameter. Stents of this type are used for the recanalization of pathologically altered hollow organs. In this respect, the stents are introduced in the compressed state via a delivery catheter to the position within the hollow organ to be treated where they are expanded by different measures to a diameter which corresponds to the diameter of the healthy hollow organ so that a support effect of the hollow organ, for example of a vessel wall, is achieved.

Such stents can e.g. be produced in that apertures such as slits are cut into the wall of a tubular body and extend partly in the longitudinal direction of the stent so that diamond-shaped apertures, for example, are produced on the expansion of the stent.

To be able to ensure this support effect, the stents must be able to exert a sufficient radial placement force which counteracts a radial force effect exerted by the vessel wall. At the same time, the stents must have a sufficient flexibility in the direction transverse to their longitudinal extent to be able to adapt to curved hollow organs such as in joint regions without there being a risk of a kinking of the stent and of a reduction or interruption of the blood flow in the blood vessel caused thereby or even of a piercing of the vessel wall.

Stents have already been proposed which comprise a plurality of support sections and connection sections or joint sections which follow one another in the longitudinal direction of the stent. The support sections in this respect each have a plurality of apertures of the wall of the tubular body and bordering elements which are formed by the tubular body, which surround the apertures and which form cells of the support sections together with them in the expanded state. Two support sections adjacent in the longitudinal direction are in this respect connected to one another via a connection section which is disposed therebetween, wherein mutually facing end faces of the adjacent support sections are each formed by a row of end-face cells of the respective support section. The connection section comprises one or more connection elements which are formed by the tubular body and which connect the mutually facing end faces of the two adjacent support sections to one another.

The connection sections in these stents can serve as a joint between the support sections determining the radial placement force of the stent and can allow an adaptation of the stent shape to a curved vessel shape since adjacent support sections are movable toward one another.

The simultaneously achievable radial placement force of the stent, on the one hand, and its flexibility transverse to the longitudinal direction, on the other hand, are also restricted in these stents in that these stents are not suitable for specific applications which require a particularly high radial placement force and simultaneously a particularly high flexibility. For example, there is a need for a stent which is suitable for deployment in the veins in particular located in the pelvic region of the body such as the vena iliaca or the vena femoralis. Such a stent has to withstand a very high radial pressure from the corresponding vessel wall and simultaneously has to have an extremely high flexibility transverse to its longitudinal direction due to the very curved shape of the named vessels.

It is the underlying object of the present invention to provide a stent of the initially named kind which is suitable for deployment in hollow organs whose support requires a high radial placement force and which simultaneously comprise very bent or curved sections such as a vein in the pelvic area of the body, with an inward kinking or a bending of the stent being reliably precluded on its deployment.

This object is satisfied in accordance with the invention, starting from a stent of the initially named kind, by the features of claim 1. The stent comprises at least two support sections which are adjacent in the longitudinal direction and which are connected to one another via a connection section disposed therebetween. In this respect, only some of the cells which form one of the two mutually facing end faces of the two adjacent support sections are connected via a connection element directly to the other one of the two mutually facing end faces of the adjacent support sections.

Since only some of the cells of the mutually facing end faces of the support sections are directly connected to the respective other end face by a connection element of the connection section, the flexibility of the stent transverse to the longitudinal direction and simultaneously its radial placement force are substantially increased since an additional support effect of the support section is admittedly effected by the cells not connected to the respective other support section, but simultaneously no stiffening is caused between the support sections which reduces the flexibility.

It was recognized in accordance with the invention that the openings in the connection section which may be comparatively large as a result of the lack of direct connections between some of the end-face cells of the adjacent support sections in the expanded stent state do not result in a reduction in the compatibility of the stent deployed in the hollow member. It was in particular recognized that, on the use of such a stent in a vein, for instance in the pelvic area of the body, larger openings in the connection sections can easily be tolerated without there being a risk of a restenosis or of other incompatibilities. A high support effect can in contrast be achieved in the support sections by the comparatively small extent of the apertures. An extent of the openings in the connection sections increased in size in comparison with the cells of the support sections is therefore deliberately accepted within the framework of the invention to achieve an increased flexibility of the stent with a simultaneously high radial placement force.

Advantageous embodiments of the invention can be seen from the dependent claims, from the description and from the Figures.

In principle, the stent can comprise more than two support sections and more than one connection section which follow one another in the longitudinal direction, wherein one connection section connects two respective support sections to one another which are mutually adjacent in the longitudinal direction. The support sections, the connection sections and the connections between two adjacent support sections via a connection section can in this respect each be configured such as is described above with respect to the at least two adjacent support sections and to the connection section disposed therebetween. When the embodiment of a support section, of a connection section or of a connection between two adjacent support sections via a connection section is described in the present description, in principle one or more support sections, and preferably all support sections, connection sections and connections between support sections can accordingly always be configured in the respective described manner. The description of the stent structure relates, where not otherwise stated, in principle to the stent with a straight orientation, that is in the non-curved state. If not otherwise stated, the stent has the respective described structure at least in the compressed state or in the expanded state and can in particular have the structure in both states.

In accordance with the invention, the end-face cells of at least one of the two adjacent support sections are only partly directly connected to the end face of the other support section via a connection element of the connection section. It is preferred for the end-face cells of both support sections connected to one another to be only partly directly connected to the other end face via a connection element.

In accordance with an advantageous embodiment, the number of connection elements of the connection section is smaller than the number of those cells of at least one of the adjacent support sections which form one of the two end faces connected to one another via the connection elements of the connection section and mutually facing one another. The number of connection elements is preferably smaller than the respective number of cells of both adjacent support sections which form the respective one of the mutually facing end faces. The number of cells forming the end faces can in this respect be the same or different for both adjacent support sections. A correspondingly small stiffness of the stent transverse to the longitudinal direction, and consequently a high flexibility of the stent, is achieved by such a small number of connection elements in comparison with the number of end-face cells. The end-face cells of one of the adjacent support sections, and preferably of both adjacent support sections, are preferably each directly connected to the respective other support section via a maximum of one connection element of the connection section.

At least one of the two adjacent support sections preferably comprises a row of cells which follow one another in the peripheral direction of the stent and which preferably form a closed ring running around in the peripheral direction of the stent. Perpendicular to the longitudinal direction of the stent, the ring preferably has a closed cross-section in annular form which is formed by the cells of the ring. An ideal radial placement force and support effect of the stent can be provided in the support section by such a ring, preferably a closed ring, running around in the peripheral direction. A ring can in principle be formed by any desired cells of the respective support section. In this respect, the cells which form the ring each cover a region of the periphery of the stent, with peripheral regions which are covered by at least some cells, and in particular by all of the cells of the ring preferably not overlapping or covering one another or at best only doing so in an insignificant manner. Viewed in the longitudinal direction, the cells are consequently arranged at least approximately completely next to one another and not behind one another. The cells which form the ring furthermore respectively cover a longitudinal region of the stent, wherein the longitudinal regions which are covered by some cells, and in particular by all the cells of the ring preferably at least approximately completely overlap or cover one another, i.e. a longitudinal region of a respective other longitudinal zone is at least completely surrounded or is surrounded thereby. Viewed in the peripheral direction, the cells are consequently arranged at least approximately completely behind one another and not next to one another. An insignificant overlap is in principle understood in this description as an overlap of up to a maximum of 20%, preferably up to 10% or up to 5% and an at least approximately complete overlap is understood as an overlap of at least 80%, preferably at least 90% or at least 95%.

As will be explained below, a support section can comprise a plurality of rows of cells which follow one another in the longitudinal direction of the stent and which each form a ring as described above. A support section can also comprise exactly one row of cells which follow one another in the peripheral direction of the stent and which preferably form a ring as described above. In particular in the last-named embodiment, both longitudinal-side end faces of the respective support section, i.e. both a front and a rear longitudinal-side end face of the support section, can be formed fully or in part by the same cells of the support section. It is in principle preferred if a ring as described above at least partly, and preferably completely, comprises cells which form at least one of the mutually facing end faces of two adjacent support sections.

In accordance with an embodiment, one or more end-face cells of a support section each have a free end which faces the respective adjacent support section or its end face. The free end of these cells preferably has a rounded shape, for example the shape of a rounded tip which represents an atraumatic rounding. An injury to the hollow organ supported by the stent can then be reliably avoided by the configuring of the free end of a cell with such an atraumatic rounding even when the free ends of the stent project slightly outwardly on a pronounced bending of the stent and are pressed into the wall of the hollow organ. The rounding can, for example, be configured approximately in circular segment shape and in particular substantially in semicircular shape.

In accordance with a further advantageous embodiment, the mutually facing end-face cells of two adjacent support sections are arranged offset from one another in the peripheral direction of the stent. The free end of an end-face cell of a support section can in this respect be arranged with respect to its position in the peripheral direction between the free ends of two end-face cells of the other support section following one another in the peripheral direction. The free ends of a plurality of end-face cells, and in particular of all end-face cells, of a support section are preferably arranged in the above-described manner such that they are arranged with respect to their position in the peripheral direction between the free ends of two end-face cells of the other support section following one another in the peripheral direction.

It can be avoided by the above-described offset of the adjacent support sections in the peripheral direction that, on a pronounced bending of the stent, the free ends of the mutually facing end faces of the adjacent support sections collide with one another or with the respective oppositely disposed end face. The risk of such a collision would otherwise be present on a pronounced bending or curvature of the stent transverse to the longitudinal direction since in this respect the end-face cells of the support section disposed at the inner side of the curvature are moved toward one another in the longitudinal direction of the stent. Due to the offset arrangement of the cells of the support sections, the free end of a cell of a support section can move into the intermediate space between two free ends of the other support section when the free ends of the support sections move toward one another as a consequence of a bending of the stent. A particularly favorable embodiment results when the free end of one or more end-face cells, and in particular all end-face cells, of a support section is arranged with respect to its position in the peripheral direction at least approximately at the center between two end-face cells of the other support section following one another in the peripheral direction or when the end-face cells of the adjacent support sections are arranged offset from one another by at least approximately half a cell width measured in the peripheral direction.

In accordance with an embodiment, at least one or more cells, and in particular all cells, of a support section are formed in substantially diamond shape in the expanded state of the stent. In the compressed state of the stent, such a cell can, for example, be formed by a slit of the tubular body which is substantially straight and which is preferably oriented in the longitudinal direction of the stent and by the bordering elements surrounding the slit. These slits can be widened as part of the expansion of the stent to form the diamond-shaped apertures. The diamonds of the expanded stent can be elongate in the longitudinal direction of the stent, that is can have a greater length than width. In the expanded state, the bordering elements of the cells defining the diamonds can be formed at least approximately straight and can, for example, respectively be oriented inclined at an angle between twenty and forty degrees, and preferably approximately thirty degrees, with respect to the longitudinal axis of the stent. A particularly high radial placement force and support effect of a support section can be achieved with such diamond-shaped cells.

In accordance with a further embodiment, at least one or more cells, and in particular all cells, of a support section have at least one section, and preferably three sections, arranged obliquely to the longitudinal axis of the stent in the expanded state of the stent. Such cells ensure an increased flexibility and bendability of the support section transverse to the longitudinal direction with a simultaneously good radial placement force. In addition to the high flexibility provided by the connection sections, in such an embodiment of the cells, the support section itself also has a relatively high flexibility transverse to the longitudinal direction of the stent so that the flexibility of the stent can be increased even further with a simultaneous maintenance of a high placement force and support effect. The described cells can be formed by one or more slits, and in particular by three slits, oriented obliquely to the longitudinal axis of the stent in the compressed state of the stent. The cells can be substantially of wave shape, in particular of sinusoidal wave shape.

In principle, it is preferred within the framework of the invention for a support section to be formed at least partly and in particular completely by closed cells. A closed cell can be formed in the compressed state of the stent by an aperture which preferably extends, with respect to the longitudinal direction of the stent, free of reversals in one direction and in particular does not form any part slits or part apertures spaced apart from one another in the peripheral direction of the stent which are arranged behind one another in an overlapping manner in the peripheral direction, i.e. which cover longitudinal regions of the stent which cover one another or overlap one another. The aperture consequently preferably does not form any undercut in the peripheral direction of the stent in the compressed state of the stent. Accordingly, the aperture can likewise form a closed surface without any undercut in the peripheral direction of the stent in the expanded state. In the compressed state of the stent, the apertures of the closed cells can substantially be of completely slit shape without any areal sections or window-like openings. The use of such closed cells results in a particularly high radial placement force and support effect of the stent in the support sections.

The one or more connection elements of the connection sections are preferably configured such that they have an increased flexibility transverse to the longitudinal direction of the stent and can be bent comparatively easily and thus provide the stent with a high flexibility. The connection elements are formed by the tubular body and can, for example, be formed by individual elongated web-shaped sections of the body as can the bordering elements of the cells of a support section. The width of the connection element can in this respect correspond to the width of the bordering elements at least sectionally and at least approximately.

In accordance with an embodiment, at least one or more connection elements, and in particular all the connection elements, of a connection section have a length measured in the longitudinal direction of the stent which amounts to at least half, and preferably at least three-quarters, of the maximum length measured in the longitudinal direction of the stent of the end-face cells of the support sections connected by the connection element. The length of the connection elements can also be at least approximately as large or larger than the length of these cells. The length of the connection element can generally amount to at least 50%, at least 75%, at least 100% or more of the maximum length of at least one end-face cell, and preferably all the end-face cells of one or both adjacent support sections. A particularly high flexibility of the connection elements transverse to the longitudinal direction of the stent is achieved by this comparatively large longitudinal extent in comparison with the cells of the support sections.

One or more connection elements, and in particular all the connection elements, of a connection section can have a relatively small angle of inclination with respect to the longitudinal axis of the stent and related to the imaginary connection line between its starting point and its end point of—in the expanded stent state—for example, between five and twenty-five degrees, and preferably approximately ten degrees. In this respect, the preferably relatively small offset, measured in the peripheral direction, between the starting point and the end point of a respective connection element can amount, for example, up to half a cell width of the support sections, measured in the peripheral direction of the stent, or up to approximately one-and-a-half times the cell width. A high flexibility of the stent in all directions perpendicular to the longitudinal axis of the stent is thereby ensured, on the one hand, and simultaneously a high stability and tensile strength in the longitudinal direction of the stent.

As described above, the end-face cells of the support sections can have free ends which face in the direction of the respective adjacent support section, which are e.g. rounded and which can be arranged offset from the free ends of the cells of the other support section. At least one or more end-face cells, and in particular all those end-face cells, of the adjacent support sections in particular also preferably have such a free end which are connected directly to the respective other support section via a connection element. A connection element can in this respect be connected in one region to an end-face cell of a support section which is spaced apart from a free end of this cell facing the respective other support section, preferably in the peripheral direction of the stent, and is preferably arranged offset to the rear with respect to the free end of the cell relative to the longitudinal direction of the stent. A connection element can in this respect be connected to the end face at least approximately in a region of the end face which is arranged set back the most to the rear relative to the longitudinal direction of the stent. The connection element can equally be arranged at least approximately at the center between the free ends of two end-face cells of a support section following one another in the peripheral direction. A longer configuration of the connection element is thereby made possible without an increase in the spacing between the two support sections being necessary overall. In this respect, as a result of the short spacing between the adjacent support sections, a very good support effect can be achieved with a simultaneously high flexibility of the stent.

In accordance with an embodiment, at least one connection element of the connection section is connected to the end face of a support section in a region in which two cells of this support section are connected to one another which form the end face and which are adjacent to one another. Such a connection region is typically arranged at the center between the free ends of the two cells, viewed in the peripheral direction, and allows a particularly long and thus flexible design of the respective connection element without the spacing between the two support sections being increased. The connection element can be located between two end-face cells of a support section with such a connection over at least a part of its length in the peripheral direction. In order in particular to provide the space required for the connection element in the compressed state of the sent, the connection region to which the connection element is connected can be widened or extended slightly in the peripheral direction, in particular approximately by the width of the connection element, with respect to a corresponding connection region between two end-face cells of the support section. Either a further connection element can in this respect be arranged at the side of the connection region remote from the connection element, in particular when the respective support section comprises exactly one ring of cells, or an aperture can be formed there which is expanded with respect to a simple slit and has a width which in particular substantially corresponds to the width of the connection element.

The connection sections respectively comprise one or more throughgoing openings of the tubular body which are bounded by one or more connection elements. An opening of the connection section is preferably bordered and surrounded by one or more connection elements and by sections of at least one and preferably both of the mutually facing end faces of the support sections connected to one another by the connection section.

The connection section preferably comprises a plurality of openings which define a plane which is oriented perpendicular to the longitudinal direction and which intersects a plurality of the openings, and preferably all of the openings, of the connection section.

The openings of the connection section in this respect each cover a region of the periphery of the stent, wherein at least some peripheral regions, and in particular all the peripheral regions, which are covered by the openings preferably do not overlap or cover one another or do so at most insignificantly. The openings are consequently arranged at least approximately completely next to one another and not behind one another in the longitudinal direction. The openings of the connection section furthermore each cover at least one longitudinal region of the stent, wherein at least some of the longitudinal regions, and preferably all of the longitudinal regions, which are covered by the openings preferably overlap or cover one another at least approximately completely, i.e. a longitudinal region at least approximately completely encompasses a respective other longitudinal region. Viewed in the peripheral direction, the openings are consequently arranged at least approximately completely behind one another and not next to one another. The openings can therefore follow one another purely in the peripheral direction and openings arranged fully or partly behind one another in the longitudinal direction are avoided in this embodiment, whereby a high flexibility is achieved with a small length of the connection section.

Corresponding to the preferably relatively small number of connection elements of the connection section, the number of the openings of the connection section is preferably smaller than the number of cells which each form one of the mutually facing end faces of the two support sections connected by the connection section. A high flexibility of the connection section is thereby ensured. In a particularly simple case, a connection section can comprise exactly one connection element, wherein the connection element can comprise exactly one opening which extends around the stent in the peripheral direction and which is bounded at both sides by the one connection element, viewed in the peripheral direction.

The flexibility of the connection sections can be increased in that one or more openings, and in particular all the openings, of the connection sections are not purely slit-shaped in the compressed state of the stent, but are at least regionally areal and form a window-like portion. One or more openings, and in particular all the openings, of the connection section can have an area, at least in the expanded state of the stent, which is larger than the respective area of one or more apertures, and in particular of all of the apertures, which belong to the end-face cells of the adjacent support sections. The area of an opening of the connection section can in this respect be at least 50%, preferably at least 100%, and particularly preferably at least 200% larger than the respective area of the apertures of the support sections. The area of the openings or apertures is in this respect defined as the part area of the outer enveloping jacket surface of the stent which is formed by the respective opening or aperture.

In accordance with an advantageous embodiment, at least connection element, and preferably a plurality of connection elements, and in particular all the connection elements, of a connection section are oriented at least sectionally transverse to the longitudinal direction of the stent. In this manner, the flexibility of the connection element transverse to the longitudinal direction of the stent can be increased, on the one hand, and an offset as described above between the cells of the adjacent support sections can be bridged in the peripheral direction, on the other hand.

One or more connection elements, and in particular all the connection elements, of a connection section can have a kinked or curved shape and can preferably be substantially S-shaped or Z-shaped. Such a shape ensures a particularly high flexibility of the connection elements transverse to the longitudinal direction of the stent.

In accordance with an embodiment, a support section has exactly one row of cells which follow one another in the peripheral direction of the stent. The row of cells can in this respect form a closed ring of the support section as described above. The cells of the one row can in this respect form both a front and a rear longitudinal-side end face of the support section. A good placement effect can be achieved using such a support section, wherein a number of such support sections respectively connected to one another via a connection section ensure a particularly high flexibility of the stent. At least one support section can, however, also have a plurality of rows of cells following one another in the longitudinal direction of the stent, wherein the cells of a row are each arranged following one another in the peripheral direction of the stent. The rows of cells in this respect preferably form a grid or grid network of cells, at least in the expanded state of the stent, repeating both in the longitudinal direction and in the peripheral direction of the stent. A row of cells of the support section following one another in the peripheral direction can in this respect each form a closed ring running around in the peripheral direction of the stent, as described above.

In accordance with an advantageous embodiment, the stent has more than two support sections and a plurality of connection sections which follow one another in the longitudinal direction of the stent, wherein a connection section connects two respective mutually adjacent support sections which follow one another in the longitudinal direction. The flexibility of the stent is improved by the provision of a plurality of support sections and connection sections which each connect two support sections. It is generally preferred for the stent to have at least three support sections, wherein one support section is located at the center of the stent, viewed in the longitudinal direction of the stent, while the other two support sections can, for example, be arranged at the longitudinal-side ends of the stent. The stent can, however, also have at least four, eight, ten, twenty or up to forty and more support sections and a corresponding number of connection sections which follow one another in the longitudinal direction of the stent.

The connection elements of two connection sections which in particular follow one another in the longitudinal direction and which are adjacent one another are preferably arranged offset from one another in the peripheral direction of the stent. A uniform flexibility of the stent in all directions perpendicular to the longitudinal direction can thereby be achieved.

In accordance with an advantageous embodiment, a support section has a larger length, measured in the longitudinal direction of the stent, than another support section. Alternatively or additionally, a support section can have a larger number of rows of cells following one another in the peripheral direction of the stent than the other support section, said rows following one another in the longitudinal direction of the stent. The stiffness of the stent in the corresponding regions can be directly increased or decreased, e.g. to achieve a desired behavior on the delivery of the stent, by the use of support sections having different lengths or different numbers of cell rows following one another in the longitudinal direction. For example, a support section, which is arranged at a longitudinal-side end of the stent, can have a larger axial length and/or a larger number of cell rows than a support section arranged in a central region in order thereby to achieve a greater stability or stiffness of the stent at the longitudinal-side end.

A connection section of the stent can, for example, have between one and ten connection elements and preferably one, two, three or four connection elements. Such a relatively small number of connection elements has proven advantageous to achieve the desired high flexibility of the stent perpendicular to the longitudinal direction of the stent.

A connection section preferably comprises a plurality of connection elements which are arranged distributed at at least approximately equal angular intervals over the periphery of the stent, wherein the angular intervals relate to the preferably approximately circular cross-section of the stent.

The end face of a support section can be formed, for example, by 4 to 42, preferably between 8 and 34, and particularly preferably between 12 and 24 cells. Such a number of cells has proven advantageous to achieve the desired high radial placement force and support effect of the stent in the support sections. These numbers are also preferred with respect to a ring of cells formed by a support section and running around the stent in the peripheral direction.

A particularly high support effect of the stent can be achieved if the substantially tubular body of the stent has a wall thickness of between 0.20 mm and 0.40 mm, preferably between 0.28 mm and 0.45 mm, and particularly preferably between 0.30 mm and 0.50 mm. The diameter of the stent in the expanded state can preferably amount to between 6 and 30 mm or between 10 and 24 mm. The length of the stent in the expanded state can amount to between 30 and 250 mm and preferably between 50 and 180 mm.

The stent is preferably configured as a self-expanding stent and can preferably comprise or consist of a shape-memory material such as nitinol.

The stent can comprise, at at least one of its longitudinal-side ends, one or more holding elements which have a neck section adjoining the remainder of the stent and a holding section connected to the remainder of the stent via the neck section and widened with respect to the neck section. These holding elements can cooperate with corresponding positioning elements of a delivery catheter to hold the stent in the desired position relative to the delivery catheter up to its release. The stent can equally have, at one or both longitudinal-side ends, one or more areal marking elements which improve the X-ray observation capability of the stent. The holding elements and the marking elements are preferably formed by the tubular body of the stent.

Figure 4:
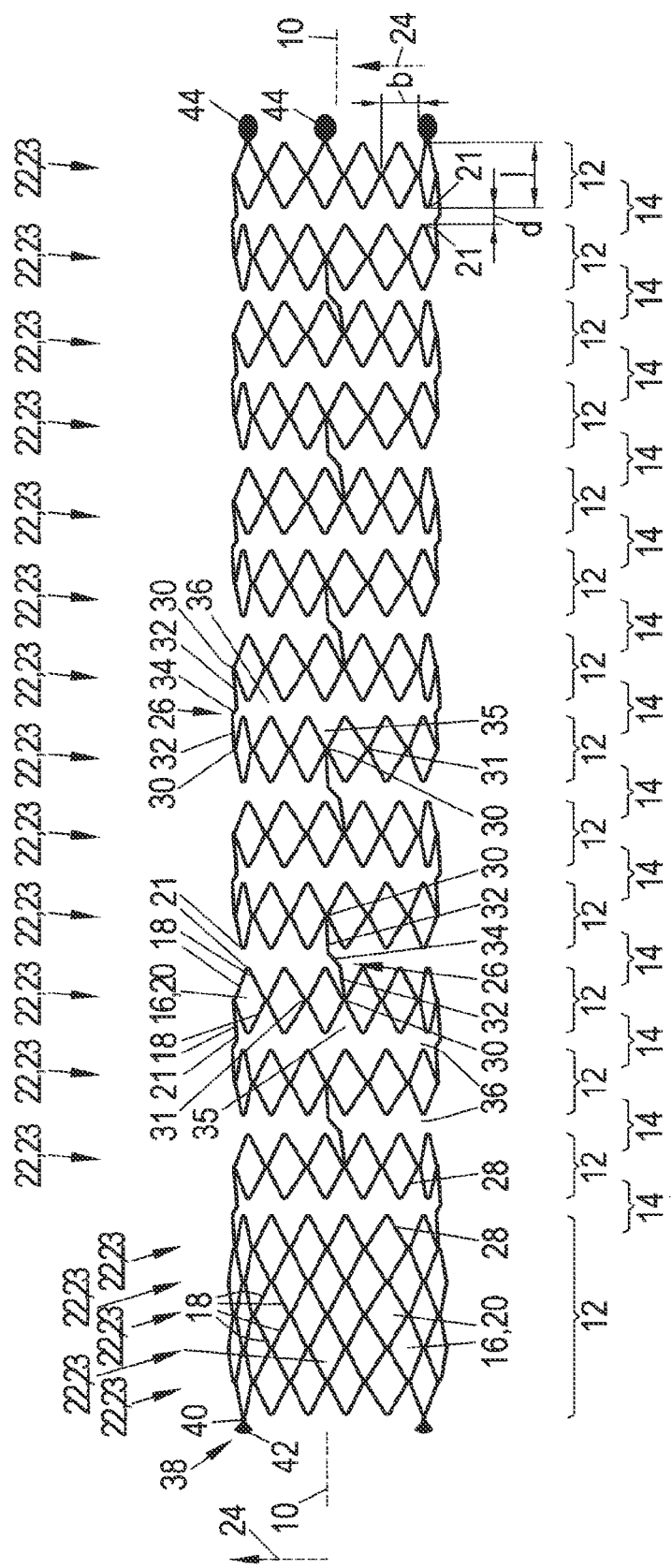
Figure 5:
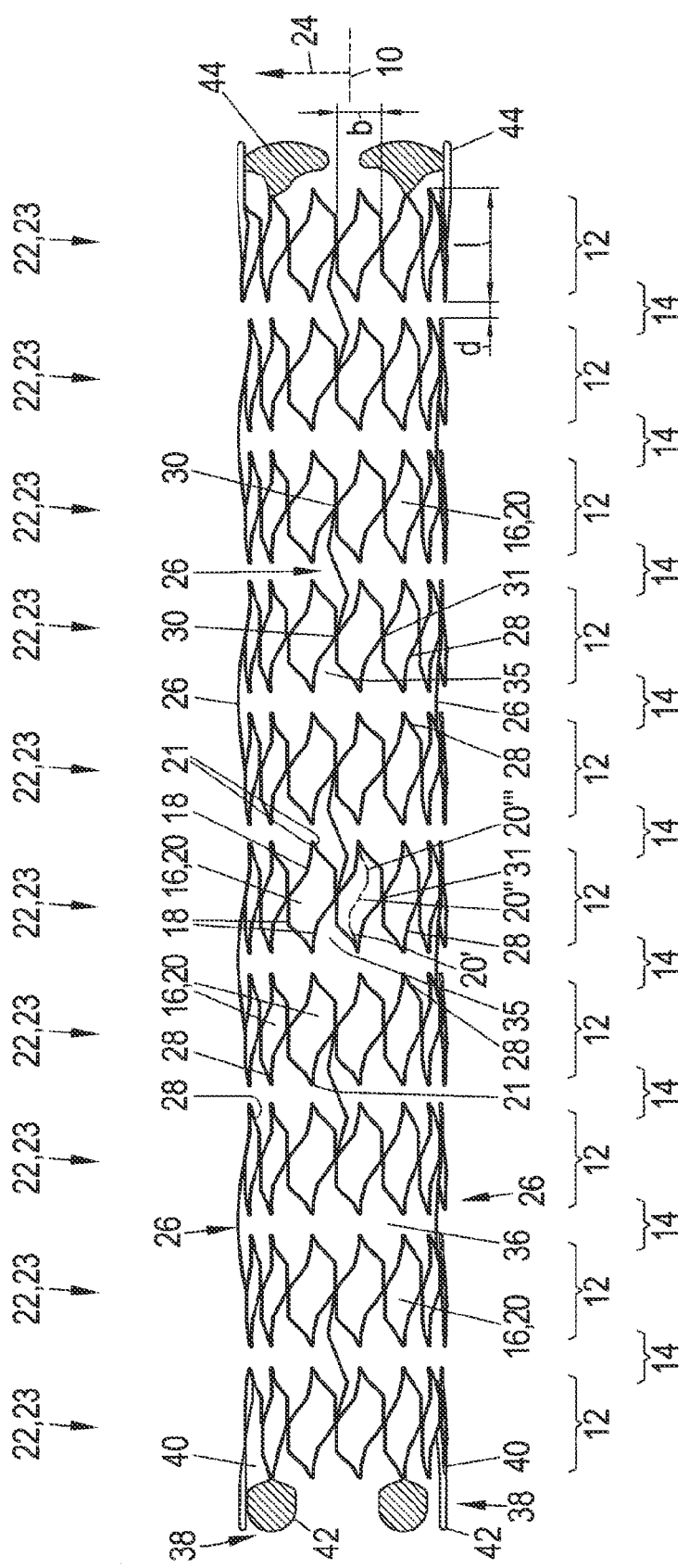
Figure 6:
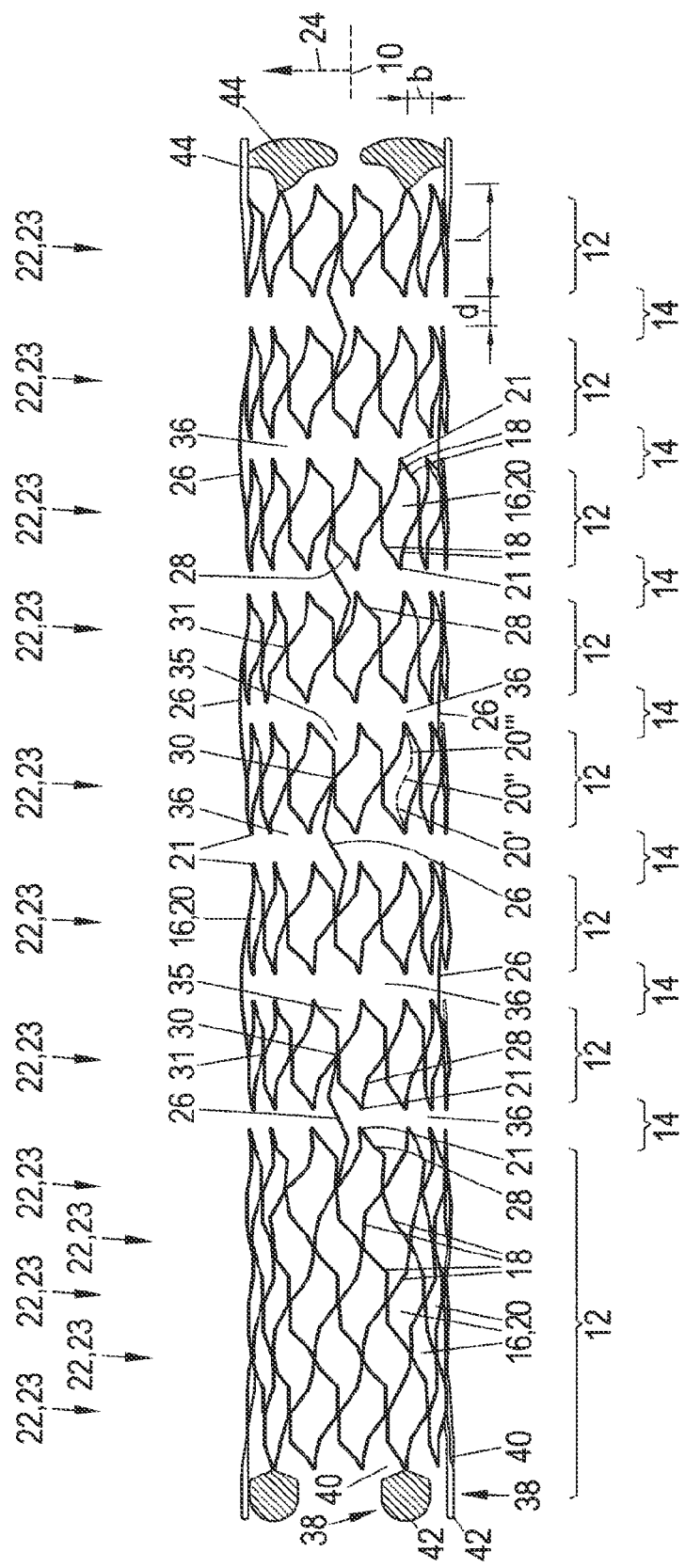

The invention will be described in the following with reference to advantageous embodiments and to the enclosed Figures. There are shown:

FIG. 1 a stent in accordance with an embodiment of the invention in the compressed state and in a representation projected into a plane;

FIG. 2 a stent in accordance with a further embodiment of the invention in the expanded state in a side view;

FIG. 3 a cell of the stent of FIG. 2;

FIG. 4 a stent in accordance with a further embodiment of the invention in the expanded state in a side view;

FIG. 5 a stent in accordance with a further embodiment of the invention in the expanded state in a side view; and FIG. 6 a stent in accordance with a further embodiment of the invention in the expanded state in a side view.

FIG. 1 shows a stent in accordance with an embodiment of the invention in the compressed state and in a representation projected into a plane or "rolled off" in the peripheral direction.

The stent formed by a tubular body is divided into a plurality of different longitudinal sections 12, 14 along its longitudinal axis 10. The stent comprises a plurality of support sections 12 and connection section 14, wherein two respective support sections 12 adjacent to one another in the longitudinal direction are connected to one another by a connection section 14 disposed therebetween.

The support sections 12 each comprise a plurality of apertures 16 which are oriented straight in the longitudinal direction 10 and which are of slit-shape in the compressed state and comprise bordering elements 18 which are formed by the tubular body, which surround the apertures 16 and which form cells 20 of the support section 12 together with them. The cells 20 have free ends 21 which are each rounded for forming an atraumatic rounding.

Each support section 12 comprises a row 22 of cells 20 which follow one another in the peripheral direction 24 of the stent and which overlap, viewed in the peripheral direction 24, at least approximately completely without overlapping viewed in the longitudinal direction 10 of the stent. The longitudinal regions respectively covered by the cells 20 of a row 22 therefore overlap one another substantially completely and cover one another, while the peripheral regions covered by the cells 20 of the row 22 do not overlap or cover one another. The rows 22 of cells 20 in this respect each form a closed ring 23 running around the stent in the peripheral direction 24. The cells 20 of adjacent support sections 12 are arranged offset from one another by half a cell width b (see also FIG. 2) in the peripheral direction 24 of the stent so that the free ends 21 do not collide on a bending of the stent perpendicular to the longitudinal axis 10.

The connection sections 14 each comprise two substantially S-shaped connection elements 26 which are formed by the tubular body of the stent and which each connect the mutually facing end faces 28 of the two support sections 12 connected to one another by the respective connection section 14 to one another. The cells 20 of a support section 12 in the present embodiment form both the front and the rear end face 28 of a support section 12 since only one row 22 of cells 20 is present. As can be seen in FIG. 1, the connection elements 26 of a connection section 14 are evenly distributed over the periphery of the stent, i.e. in the present embodiment with two connection elements 26 per connection section 14 at an angular interval of 180 degrees with respect to one another.

The connection elements 26 are each connected to the end faces in a region 30 of the end faces 28 in which two cells 20 of the respective support sections 12 following one another in the peripheral direction 24 are connected to one another and merge into one another. The regions 30 of two adjacent support sections 12 in which a connection section 26 is respectively connected to the support sections 12 are arranged offset from one another by one-and-a-half cell widths b in the peripheral direction 24. FIG. 2 in contrast shows an embodiment in which the regions 30 of the support sections 12 to which the two ends of a connection element 26 are connected are offset from one another by half a cell width b in the peripheral direction 24.

The connection elements 26 have, as shown in FIG. 1, two respective straight sections 32 which are oriented in the longitudinal direction 10 in the compressed state of the stent and which are each connected to one of the regions 30 and have a section 34 which is arranged between the sections 32, which is inclined with respect to the longitudinal direction 10 and which has an extent in the peripheral direction 24 which corresponds to 1.5 times the cell width b and which thus corresponds to the peripheral offset between the mutually connected regions 30. The sections 32 each extend between bordering elements 18 of the cells 20 connected by the connection region 30. To provide the space required for the sections 32, the connection regions 30 which are connected to a connection element 26 are widened in the peripheral direction with respect to the connection regions 31 of two cells 22 which are adjacent in the peripheral direction 24 and which are not connected to a connection element 26. The regions 30 are specifically widened with respect to the regions 31 by the width of the respective section 32 of the connection element 26 which corresponds approximately to the width of a bordering element 18, i.e. b/2 in FIG. 1. A further connection element 26 could in principle be arranged at the side of the connection region 30 remote from the connection element 26. In the present embodiment, areally cut-out regions 35 are arranged at the sides of the connection regions 30 remote from the respective connection element 26, said cut-out regions extending in the longitudinal direction 10 between the bordering elements 18 of the adjacent cells in the compressed state of the stent and approximately having the shape of a section 32 of a connection element 26, i.e. in particular approximately having the width of a bordering element 18.

As shown in FIG. 2, the sections 32 of the connection elements 25 oriented in parallel with the longitudinal section 10 in the compressed state are also slightly inclined with respect to the longitudinal direction 10 as a result of the expansion in the expanded state of the stent.

The two sections 32 oriented in parallel with the longitudinal direction 10 in the compressed state are approximately as long as half a cell length l, viewed in the longitudinal direction 10, so that a total length of a connection element 26 results, together with the central section 34, which is somewhat larger than the cell length l and bridges a spacing d between the two adjacent support sections 12. As shown in FIG. 1, openings 36 of the connection section 14 are formed between the connection elements 26 and comprise areally cut-out regions, including the regions 35, in addition to simply slit regions in the compressed stent state.

The connection elements 26 of two respective connection sections 14 following one another in the longitudinal direction are arranged offset from one another in the peripheral direction 24 so that the connection elements 26 of a connection section 14 are disposed at the center, viewed in the peripheral direction 24, between two connection elements 26 of the other connection section 14. The connection elements 26 of the same connection 14 are specifically each offset by a peripheral angle of 180° from one another and in each case by a peripheral angle of 90° from the connection elements 26 of the connection section 14 adjacent in the longitudinal direction 10. In addition, the direction of the peripheral offset bridged by the connection elements 26 reverses between the regions 30 respectively connected by the connections elements 26 from one connection section 14 to the next. That means that while e.g. in FIG. 1 the connection elements 26 of the connection section 14 arranged furthest to the left each run from the bottom left to the top right between two regions 30, the connection elements 26 of the connection section 14 following on in the longitudinal direction 10 each extend from the top left to the bottom right between two regions 30.

A respective plurality of holding elements 38 are arranged at the longitudinal-side ends of the stent and have a neck section 40 and a holding section 42 widened with respect thereto. These holding elements 38 are likewise formed by the tubular body of the stent and serve for fixing the stent to a positioning element, in particular to a ring-shaped positioning element, of a delivery catheter which has openings, for example, into which the holding elements 38 engage in the state of the stent fixed to the delivery catheter, wherein the holding elements 38 can form undercuts oriented in the longitudinal direction 10 with the positioning element for fixing the stent.

FIG. 2 shows a stent in accordance with a further embodiment of the invention which substantially corresponds to the stent shown in FIG. 1. FIG. 2 in this respect shows a side view of the tubular expanded stent, wherein for better clarity only the components of the stent are shown which are disposed at the front in the direction of view and the rear side of the stent is not shown.

In the expanded state of the stent shown in FIG. 2, the cells 20 are widened in the peripheral direction 24 to form diamonds. In FIG. 2, the offset directed in the peripheral direction 24 and amounting to half a cell width b between the cells 20 of two support sections 12 following one another can also be seen which prevents a collision of the free ends 21 of the cells 20 on a bending of the stent in the direction perpendicular to the longitudinal direction 10.

FIG. 3 shows an enlarged representation of a cell 20 of the stent sown in FIG. 1 or 2 in the expanded state, including the aperture 16, of the bordering elements 18 surrounding the aperture 16 and of the rounded free ends 21. The bordering elements 18 are in this respect substantially straight and include an angle α of approximately 30° with the longitudinal direction 10 of the stent. A very high radial placement force and support effect of the stent in the support sections 12 is achieved by this shape.

FIG. 4 shows a stent in accordance with a further embodiment of the invention which substantially corresponds to the stent shown in FIG. 2. The support section 12 arranged at the longitudinal-side end shown at the left in FIG. 4 is in this respect, however, not formed like the other support sections 12 only by one row 22 of cells 20 following on from one another in the peripheral direction 24, but rather by a total of five rows 22 of cells 20 which follow one another in the longitudinal direction 10 and which together form a diamond grid network in which the cells 20 repeat regularly both in the longitudinal direction 10 and in the peripheral direction 24. In the compressed state, these apertures 16 form regularly repeating slits in the longitudinal direction 10 and the peripheral direction 24.

FIG. 5 shows a stent in accordance with a further embodiment of the invention which substantially corresponds to the stent shown in FIG. 3. However, in this embodiment, the cells 20 of the support sections 12 are substantially of S shape or of wave shape and each comprise three sections 20', 20", 20''' oriented obliquely to the longitudinal axis 10 of the stent in the expanded and compressed states. In the embodiment shown in FIG. 5, the cells 20 of support sections 12 following one another in the longitudinal direction 10 are not arranged offset from one another in the peripheral direction 24 so that the free ends 21 of the cells 20 of the mutually facing end faces 28 are directly opposite one another. However, an embodiment as shown in FIGS. 3 and 4 is also possible here in which the cells 20 are, for example, arranged offset by half a cell width b from one another in the peripheral direction 24. Accordingly, the Z-shaped connection elements 26 of the stent shown in FIG. 5 could be connected in regions 30 to the end faces 28 of the support sections 12 which are arranged offset from one another in the peripheral direction 24, for example by half a cell width, one cell width or one-and-a-half cell widths b, instead of being connected as shown in FIG. 5 to regions 30 disposed on a line in the longitudinal direction 10.

FIG. 6 shows a stent in accordance with a further embodiment of the invention which substantially corresponds to the stent shown in FIG. 5. In this respect, the support section 12 of the stent shown furthest to the left in FIG. 6, however, has five rows 22 following one another in the longitudinal direction 10 of cells 20 which follow one another in the peripheral direction 24 and which form a grid network of wave-shaped cells 20 repeating in the longitudinal direction 10 and the peripheral direction 24. The stiffness of the stent in the end region shown at the left in FIG. 6 is thereby increased.

REFERENCE NUMERAL LIST 10 longitudinal axis, longitudinal direction
12 support section
14 connection section
16 aperture
18 bordering element
20 cell
20', 20", 20''' section
21 free end
22 row
23 ring
24 peripheral direction
26 connection element
28 end face
30, 31 connection region
32, 34 section of a connection element
35 areally cut-out region
36 opening
38 holding element
40 neck section
42 holding section
44 marking element
α angle
b cell width
d spacing
l cell length

The invention claimed is:

1. A stent for transluminal implantation into hollow organs, having a substantially tubular body which can be converted from a compressed state having a first cross-sectional diameter into an expanded state having an enlarged second cross-sectional diameter,
wherein the stent comprises at least two support sections and at least one connection section which follow one another in the longitudinal direction of the stent;
wherein the support sections each have a plurality of apertures of the wall of the tubular body and bordering elements which are formed by the tubular body, which surround the apertures and which form cells of the support sections together with them in the expanded state;
wherein two support sections adjacent in the longitudinal direction are connected to one another via a connection section disposed therebetween;
wherein mutually facing end faces of the adjacent support sections are each formed by a row of end-face cells of the respective support section;
wherein the connection section comprises one or more connection elements which are formed by the tubular body and which connect the mutually facing end faces of the two adjacent support sections to one another,
and wherein only some of the cells, which form one of the two mutually facing end faces of the adjacent support sections, are directly connected to the other one of the two mutually facing end faces of the adjacent support sections via a connection element,
wherein the stent comprises an end-side support section arranged at the stent's longitudinal-side end and a central region of the stent adjoining this end-side support section,
wherein the central region of the stent is formed by a plurality of support sections which are adjacent in the longitudinal direction, which are connected to one another by connection sections and which each have exactly one row of cells which follow one another in the peripheral direction of the stent; and
wherein the end-side support section has a plurality of rows of cells following one another in the longitudinal direction of the stent, with the cells of a row each being arranged following one another in the peripheral direction of the stent, so that the end-side support section has a larger axial length and a larger number of rows of cells following one another in the peripheral direction of the stent than the support sections arranged in the central region of the stent, said rows following one another in the longitudinal direction of the stent; and wherein the mutually facing end-face cells of two adjacent support sections are arranged offset from one another in the peripheral direction of the stent.

2. The stent in accordance with claim 1,
wherein the number of connection elements of the connection section is smaller than the number of those cells of at least one of the adjacent support sections which form one of the two mutually facing end faces connected to one another via the connection elements of the connection section.

3. The stent in accordance with claim 1,
wherein at least one adjacent support section comprises a row of cells which follow one another in the peripheral direction of the stent.

4. The stent in accordance with claim 3,
wherein the row of cells which follow one another in the peripheral direction of the stent form a closed ring running around in the peripheral direction of the stent.

5. A stent for transluminal implantation into hollow organs, having a substantially tubular body which can be converted from a compressed state having a first cross-sectional diameter into an expanded state having an enlarged second cross-sectional diameter,
   wherein the stent comprises at least two support sections and at least one connection section which follow one another in the longitudinal direction of the stent,
   wherein the support sections each have a plurality of apertures of the wall of the tubular body and bordering elements which are formed by the tubular body, which surround the apertures and which form cells of the support sections together with them in the expanded state;
   wherein two support sections adjacent in the longitudinal direction are connected to one another via a connection section disposed therebetween;
   wherein mutually facing end faces of the adjacent support sections are each formed by a row of end-face cells of the respective support section;
   wherein the connection section comprises one or more connection elements which are formed by the tubular body and which connect the mutually facing end faces of the two adjacent support sections to one another;
   wherein only some of the cells, which form one of the two mutually facing end faces of the adjacent support sections, are directly connected to the other one of the two mutually facing end faces of the adjacent support sections via a connection element;
   wherein the stent comprises an end-side support section arranged at the stent's longitudinal-side end and a central region of the stent adjoining this end-side support section,
   wherein the central region of the stent is formed by a plurality of support sections which are adjacent in the longitudinal direction, which are connected to one another by connection sections and which each have exactly one row of cells which follow one another in the peripheral direction of the stent;
   wherein the end-side support section has a plurality of rows of cells following one another in the longitudinal direction of the stent, with the cells of a row each being arranged following one another in the peripheral direction of the stent, so that the end-side support section has a larger axial length and a larger number of rows of cells following one another in the peripheral direction of the stent than the support sections arranged in the central region of the stent, said rows following one another in the longitudinal direction of the stent; and
   wherein the all of the cells forming the end face of a support section each have a free end which faces the respective adjacent support section and which has a rounded shape.

6. The stent in accordance with claim 1,
wherein the cells of the support sections are substantially diamond-shaped in the expanded state of the stent.

7. The stent in accordance with claim 1,
wherein the cells of the support sections have at least one section arranged obliquely to the longitudinal axis of the stent.

8. The stent in accordance with claim 1,
wherein at least one connection element of the connection section has a length measured in the longitudinal direction of the stent in the expanded and/or compressed state of the stent which amounts to at least 50% or more of the length of the cells connected by the connection element.

9. A stent for transluminal implantation into hollow organs, having a substantially tubular body which can be converted from a compressed state having a first cross-sectional diameter into an expanded state having an enlarged second cross-sectional diameter,
   wherein the stent comprises at least two support sections and at least one connection section which follow one another in the longitudinal direction of the stent;
   wherein the support sections each have a plurality of apertures of the wall of the tubular body and bordering elements which are formed by the tubular body, which surround the apertures and which form cells of the support sections together with them in the expanded state;
   wherein two support sections adjacent in the longitudinal direction are connected to one another via a connection section disposed therebetween;
   wherein mutually facing end faces of the adjacent support sections are each formed by a row of end-face cells of the respective support section;
   wherein the connection section comprises one or more connection elements which are formed by the tubular body and which connect the mutually facing end faces of the two adjacent support sections to one another;
   wherein only some of the cells, which form one of the two mutually facing end faces of the adjacent support sections, are directly connected to the other one of the two mutually facing end faces of the adjacent support sections via a connection element;
   wherein the stent comprises an end-side support section arranged at the stent's longitudinal-side end and a central region of the stent adjoining this end-side support section,
   wherein the central region of the stent is formed by a plurality of support sections which are adjacent in the longitudinal direction, which are connected to one another by connection sections and which each have exactly one row of cells which follow one another in the peripheral direction of the stent;
   wherein the end-side support section has a plurality of rows of cells following one another in the longitudinal direction of the stent, with the cells of a row each being arranged following one another in the peripheral direction of the stent, so that the end-side support section has a larger axial length and a larger number of rows of cells following one another in the peripheral direction of the stent than the support sections arranged in the central region of the stent, said rows following one another in the longitudinal direction of the stent; and wherein at least one connection element of the connection section is connected to the end face of a support section in a region in which two cells of this support section forming the end face are connected to one another.

10. The stent in accordance with claim 1,
wherein at least one connection element of the connection section is oriented at least sectionally transverse to the longitudinal direction of the stent.

11. The stent in accordance with claim 1,
wherein the at least one connection element of the connection section has a kinked or curved shape.

12. The stent in accordance with claim 11,
wherein the at least one connection element of the connection section is substantially of S shape or of Z shape.

13. The stent in accordance with claim 1,
wherein the stent has more than two support sections and a plurality of connection sections which follow one another in the longitudinal direction of the stent, with a connection section respectively connecting two mutually adjacent support sections to one another.

14. The stent in accordance with claim 13,
wherein the connection elements of two connection sections are arranged offset from one another in the peripheral direction of the stent.

15. The stent in accordance with claim 13,
wherein the connection elements of two connection sections adjacent to one another are arranged offset from one another in the peripheral direction of the stent.

16. A stent for transluminal implantation into hollow organs, having a substantially tubular body which can be converted from a compressed state having a first cross-sectional diameter into an expanded state having an enlarged second cross-sectional diameter, wherein the stent comprises at least two support sections and at least one connection section which follow one another in the longitudinal direction of the stent;

wherein the support sections each have a plurality of apertures of the wall of the tubular body and bordering elements which are formed by the tubular body, which surround the apertures and which form cells of the support sections together with them in the expanded state;

wherein two support sections adjacent in the longitudinal direction are connected to one another via a connection section disposed therebetween;

wherein mutually facing end faces of the adjacent support sections are each formed by a row of end-face cells of the respective support section;

wherein the connection section comprises one or more connection elements which are formed by the tubular body and which connect the mutually facing end faces of the two adjacent support sections to one another;

wherein only some of the cells, which form one of the two mutually facing end faces of the adjacent support sections, are directly connected to the other one of the two mutually facing end faces of the adjacent support sections via a connection element;

wherein the stent comprises an end-side support section arranged at the stent's longitudinal-side end and a central region of the stent adjoining this end-side support section, wherein the central region of the stent is formed by a plurality of support sections which are adjacent in the longitudinal direction, which are connected to one another by connection sections and which each have exactly one row of cells which follow one another in the peripheral direction of the stent;

wherein the end-side support section has a plurality of rows of cells following one another in the longitudinal direction of the stent, with the cells of a row each being arranged following one another in the peripheral direction of the stent, so that the end-side support section has a larger axial length and a larger number of rows of cells following one another in the peripheral direction of the stent than the support sections arranged in the central region of the stent, said rows following one another in the longitudinal direction of the stent; and wherein the at least one connection section comprises exactly two connection elements.

17. The stent in accordance with claim 1,
wherein the at least one connection section comprises a plurality of connection elements which are arranged at at least approximately the same angular intervals distributed over the periphery of the stent.

18. The stent in accordance with claim 1,
wherein at least one end face of a support section is formed by between two and forty cells.

* * * * *